United States Patent [19]

Knee et al.

[11] Patent Number: 4,544,768

[45] Date of Patent: Oct. 1, 1985

[54] REDUCTION OF ACRYLAMIDE AND ACRYLONITRILE EMISSIONS

[75] Inventors: William R. Knee; Sergio S. Cutié, both of Midland, Mich.

[73] Assignee: The Dow Chemical Company, Midland, Mich.

[21] Appl. No.: 634,238

[22] Filed: Jul. 25, 1984

[51] Int. Cl.$^4$ .......................................... C07C 103/133
[52] U.S. Cl. ..................................... 564/206; 564/204
[58] Field of Search .......................................... 564/206

[56] References Cited

U.S. PATENT DOCUMENTS

| | | | |
|---|---|---|---|
| 2,840,611 | 6/1958 | Bikales et al. | 564/206 |
| 3,776,957 | 12/1973 | Newkirk | 564/206 |
| 3,855,075 | 12/1974 | Nachtigall | 564/206 X |
| 3,923,741 | 12/1975 | Asano et al. | 564/206 |
| 3,947,518 | 3/1976 | Ohshima et al. | 564/206 |
| 4,345,101 | 8/1982 | Asano et al. | 564/206 |

*Primary Examiner*—Paul F. Shaver
*Attorney, Agent, or Firm*—C. J. Enright

[57] ABSTRACT

A method comprising contacting a vapor stream resulting from air sparging of aqueous acrylamide containing acrylonitrile with sufficient activated carbon adsorbent to substantially remove acrylamide and acrylonitrile from the vapor stream. This is a particularly advantageous method when aqueous acrylamide is stored in remote locations.

6 Claims, 1 Drawing Figure

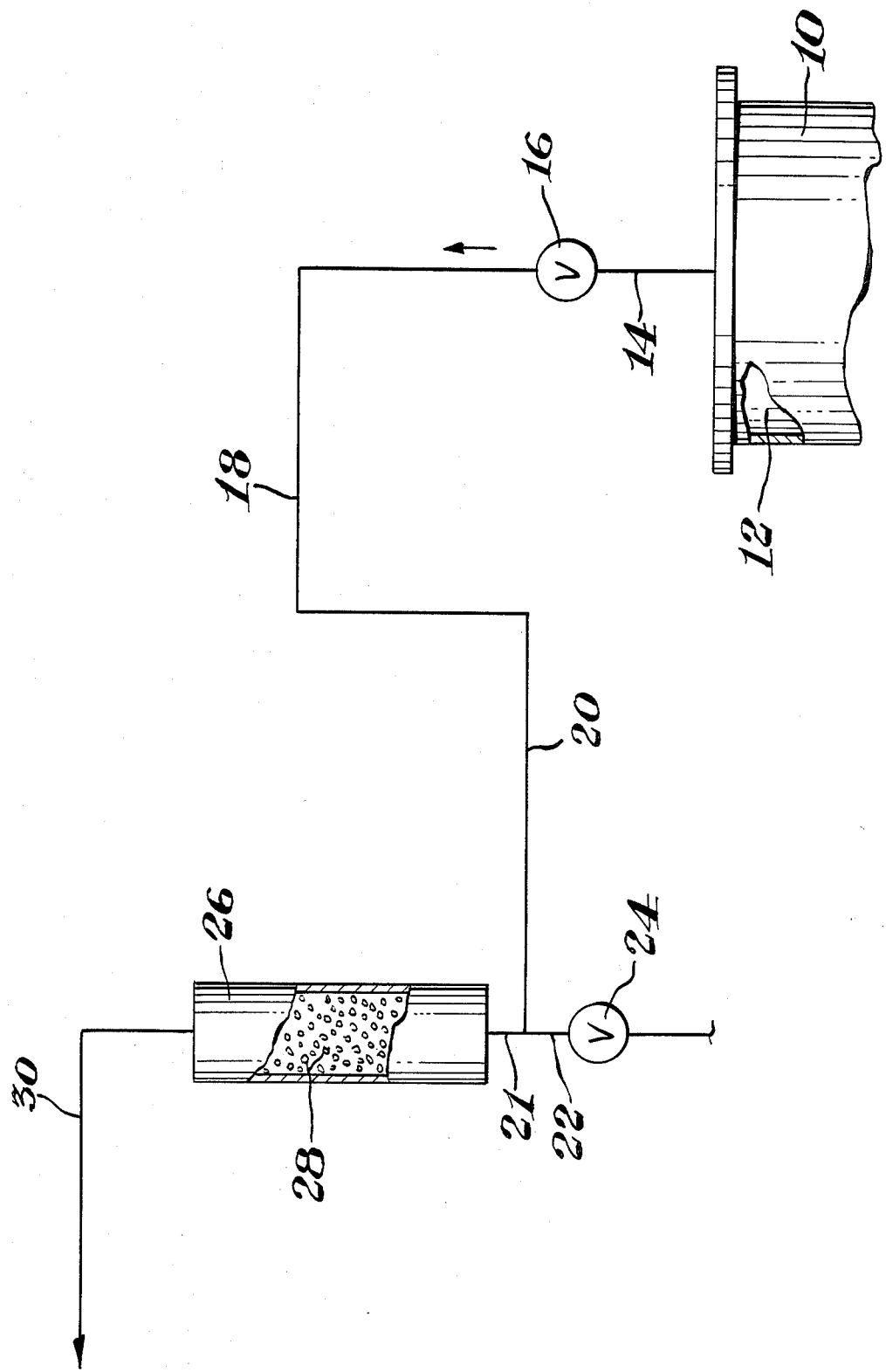

REDUCTION OF ACRYLAMIDE AND ACRYLONITRILE EMISSIONS

BACKGROUND OF THE INVENTION

Field of the Invention

This invention relates to a method of removing acrylonitrile and acrylamide contained in an air stream used to sparge aqueous acrylamide, said air stream being used to prevent polymerization of the acrylamide.

The Problem

Certain vinyl monomers such as acrylamide have a tendency to polymerize spontaneously. In order to avoid this autopolymerization, inhibitors are added to aqueous solutions of acrylamide. A widely accepted inhibitor is the combination of cupric ion dissolved in the aqueous acrylamide and a concurrent contact with oxygen in the air. This is a commercially accepted method and may be used to safely store acrylamide for periods of several months. In fixed storage vessels, usually at either acrylamide production facilities or acrylamide polymerization facilities, air is sparged or bubbled through the aqueous acrylamide solution. Typically, the air, after it has been sparged through the aqueous acrylamide solution, contains acrylamide and acrylonitrile vapors. Due to the presence of acrylonitrile impurities in the acrylamide, some acrylonitrile might also be present in the effluent air. The effluent air may be contacted with water which absorbs the acrylamide and acrylonitrile and the water may be reused to either make the acrylamide or as part of the water used in the polymerization process. Accordingly, little if any, acrylamide or acrylonitrile is emitted into the air.

For short periods of time, while aqueous acrylamide is in transit, either in rail cars or in tank trucks, it is sufficient to maintain air in the vapor space above the aqueous acrylamide to prevent polymerization. For short times, on the order of a week or two, diffusion from the vapor space is sufficient to maintain the necessary oxygen concentration in the aqueous acrylamide.

Both of these methods are unsatisfactory for situations where aqueous acrylamide monomer is held in transit for extended periods of time. Exemplary is the storage necessary for acrylamide used in on-site polymerization facilities used for enhanced oil recovery. A reliable source of supply of the acrylamide monomer is necessary for enhanced oil recovery because monomer is polymerized and injected directly into a stimulation well. Interruptions in polymer injection caused by interruptions in monomer supply can damage an enhanced recovery program. Accordingly, substantial monomer may be stored in the general vicinity of the polymerization facility.

Rather than investing the capital in a large fixed storage facility, it is often desirable to store the acrylamide monomer in the rail cars in which it is being delivered. It may be necessary to store the rail cars at locations remote from both the monomer manufacturing facility and the in-field polymerization facility. If the rail cars are stored for any substantial period of time, diffusion of oxygen from the air in the head space in the tank car is insufficient to prevent spontaneous polymerization of the acrylamide. Simply sparging air through the aqueous acrylamide is sufficient to prevent spontaneous polymerization but may be environmentally undesirable because of emissions of acrylamide and/or acrylonitrile.

OBJECTS OF THE INVENTION

It is an object of this invention to provide a satisfactory method to prevent the polymerization of aqueous acrylamide monomer in an environmentally sound manner when the acrylamide is being stored in a location remote from either a production or polymerization facility or where water scrubbing of the effluent air stream is impracticable, while at the same time preventing emissions of acrylamide or acrylonitrile into the environment.

SUMMARY OF THE INVENTION

The invention comprises a method for preventing polymerization of aqueous acrylamide in a tank, tank car or truck comprising passing an oxygen-containing gas through the aqueous acrylamide and then contacting the resulting gas stream with a carbon adsorbent.

BRIEF DESCRIPTION OF THE FIGURE

The single FIGURE is a schematic diagram of apparatus suitable for use in the process of the invention.

DETAILED DESCRIPTION OF THE INVENTION

Acrylamide is a known industrial chemical. It is most often sold or transported as a 50 percent weight aqueous solution. The aqueous acrylamide has certain typical properties and includes impurities, additives and a propensity to autopolymerize.

As an artifact of the methods used to produce acrylamide, it often contains 0.1 to 1000 ppm acrylonitrile as an impurity. Acrylonitrile is present more typically in 5–30 ppm concentration.

Autopolymerization is prevented by a combination of cupric ion and dissolved oxygen in the acrylamide. Cupric ion may be present at from about 2 to 25 or more parts per million. Preferably, the copper is present at from about 12 to about 25 ppm. Copper concentrations above 25 ppm do not seem to provide additional benefit.

Dissolved oxygen may be maintained at above about 2 ppm up to about saturation level. Saturation with dissolved oxygen occurs at about 10 ppm and is preferred. Saturation of the aqueous acrylamide may be maintained by continuous or intermittent sparging with an oxygen-containing gas such as air. The recommended air sparging rate is about 0.2 standard cubic feet per minute per 1000 gallons of aqueous acrylamide.

Remote vessels include, for example, tanks, rail cars, tank trucks or other storage vessels. The air used as sparging gas will pick up organics that may be removed by the method of the invention. The method of the invention is particularly advantageous for mobile vessels which may be stored in remote locations such as at a siding or terminal for extended periods of time.

Stored aqueous acrylamide should be maintained between about 60° F. and about 120° F. Below 60° F., acrylamide crystallizes out of a 50 percent solution. Above 120° F., autopolymerization is much more likely to occur. The pH of the solution should be maintained between about 4 and about 7 and preferably between about 5 and about 6.5 acids and bases catalyze the polymerization.

Use of zinc, aluminum, nickel or even copper in the remote vessel in contact with the aqueous acrylamide should be avoided. These metals may react with and remove the copper ion. Stainless steel, iron-free glass, natural rubber, high bake phenolic plastics and polyethylene may suitably be used as vessels or linings for vessels.

With reference to the FIGURE, apparatus useful in the method of the invention is disclosed. Aqueous acrylamide is stored in a vessel 10 only partially shown. The portion shown represents the upper hatch portion of a rail car.

Air is passed into the rail car and agitates the aqueous acrylamide stored there. In passing through the aqueous acrylamide, the air becomes saturated with water vapor and contaminated with residual acrylamide and acrylonitrile present. Beneficially, the aqueous acrylamide becomes saturated with oxygen.

The air, after passing through the aqueous acrylamide, accumulates in a vapor space 12 inside the top of the vessel 10. From there it passes through the conduit 14, valve 16, conduits 18, 20 and 21, carbon-filled cartridge 26 and conduit 30, and thence to the atmosphere.

Valve 16 may be used to block in the vessel 10 when sparging is not taking place or may be closed in order to remove or replace the cartridge 26. It is normally left open when sparging is taking place in order to avoid a pressure buildup within the vessel 10.

Conduits 18, 20 and 21 form a liquid trap system with portion 20 as the low point receiving condensed liquids. This may occur when the air leaving vessel 10 is saturated and is cooled in conduits in contact with cooler ambient conditions. To prevent condensation, an external heater, such as an electrical heating tape and/or insulation can be applied.

Accumulated liquids may be removed from the conduit 20 by opening the valve 24 which allows the fluid to exit via conduit 22. Fluids removed may be recycled to the vessel 10 but are preferably disposed of in an environmentally sound manner.

Conduit 21 includes a more or less vertical rise to insure the effectiveness of the liquid trap and to prevent carryover of liquid into the cartridge 26. Vapors pass into the cartridge 26 where particulate carbon 28 preferentially absorbs the acrylamide and acrylonitrile vapors.

The cartridge or vessel 26 contains a particulate carbon 28 which is preferably a granulated activated carbon. Suitable activated carbons are disclosed in *Encyclopedia of Chemical Technology*, Kirk-Othmer Ed., 3rd Ed., Vol. 4, pp. 561-569, John Wiley & Sons, New York (1978). This reference is incorporated herein by reference.

Preferred are those described as gas-phase carbons which have higher surface areas 1000-2000 m²/g, larger particle sizes, greater strength and density than liquid-phase carbons. By gas-phase carbons, it is meant that the carbon is more suitable for gas-phase adsorption. Exemplary carbons are activated granular coals, pelleted cokes and granular coconut shell carbons. Coconut shell carbons are preferred and Activated Carbon PCB 6X16 available from Calgon Corporation, Pittsburgh, Pennsylvania is particularly useful.

It is advantageous to use a carbon having a high capacity for acrylamide and acrylonitrile. Because the method is generally practiced in remote locations, it is often not beneficial to attempt to regenerate the carbon. Transporting the small amounts of carbon to and from the regeneration site may be prohibitively expensive. Accordingly, one full use of the cartridge, followed by disposal in an environmentally sound manner may be the better course.

At a rate of 0.2 standard cubic feet per minute per 1000 gallons of aqueous acrylamide, 4 pounds of coconut shell activated carbon may adsorb carried-over acrylamide and acrylonitrile for a week on a 20,000 gallon railroad tank car. Acrylonitrile break-through usually occurs prior to acrylamide break-through. Break-through is defined as occurring when the effluent from the carbon bed contains a significant fraction of the concentration of the contaminant vapor going into the bed.

Typical vapor concentrations exiting a typical sparged vessel are about 150-200 ppm acrylamide and about 30-50 ppm acrylonitrile in air saturated with water vapor. Removal of these contaminants may be effected to non-detectable limits before break-through.

In typical tests for acrylamide and acrylonitrile in air, with a 30-minute sampling period, detectability limits are about 0.6 ppm and about 2 ppm, respectively. Samples are taken by passing 0.1 liter per minute of the air sampled over an adsorbent for the prescribed period of time. The contaminants are then chemically removed from the adsorbent and quantified by liquid and gas chromatography.

Acrylamide and acrylonitrile vapors may be removed with an efficiency of 90 percent and preferably 99 percent using the method of the invention.

One may increase the time between cartridge changes by decreasing sparge gas flow, by intermittently sparging the aqueous acrylamide, for example, by alternating two hours on and two hours off, or by increasing the amount of carbon used as an adsorbent.

EXAMPLES

A study of the time for break-through is conducted. A 20,000-gallon railroad tank car is modified to accept an activated carbon cartridge containing four pounds of Calgon Activated Carbon PCB 6X16. Air is sparged through the 50 percent aqueous acrylamide at a rate of 7 SCF per minute and then passed through the bed of activated carbon. Samples of vapor before and after the carbon bed are taken. The samples are taken over 30 minutes at 0.1 liter per minute to yield 3 liters of vapor. The adsorbent is silica gel for acrylamide and activated carbon for acrylonitrile. The acrylamide and acrylonitrile are then removed and quantified by liquid and gas chromatography using known methods.

Table I shows the quantities of contaminants one may detect over time.

TABLE I

| Time (days) | Before Carbon Adsorption | | After Carbon Adsorption | |
|---|---|---|---|---|
| | AAm* (mg) | AN** (mg) | AAm* (mg) | AN** (mg) |
| 1 | 0.31 | 0.18 | ND[1] | ND |
| 2 | 0.80 | 0.19 | ND | 0.01 |
| 3 | 0.89 | 0.19 | ND | 0.03 |
| 4 | 0.65 | 0.18 | ND | 0.11 |
| 5 | 0.45 | | ND | |
| 6 | 0.65 | | ND | |
| 7 | 0.16 | | ND | |
| 8 | 0.8 | | ND | |
| 9 | 0.73 | | ND | |
| 12 | 1.31 | | ND | |

*AAm = Acrylamide
**AN = Acrylonitrile
[1]ND = Non-detectable 0.002 mg for AAm 0.006 mg for AN Since the acrylonitrile breaks through before the acrylamide, one may study the method by measuring only the acrylonitrile. The experiment may be repeated at a lower sparge gas throughput of 4 SCF per minute with all other variables the same. The results are set out in Table II.

TABLE II

| Time (days) | Acrylonitrile (mg) | |
|---|---|---|
| | Before Carbon Adsorption | After Carbon Adsorption |
| 0 | 0.10 | ND |
| 1 | 0.17 | ND |
| 2 | 0.16 | ND |
| 3 | 0.13 | ND |
| 4 | 0.12 | ND |
| 5 | 0.10 | ND |
| 6 | 0.14 | ND |
| 7 | 0.19 | 0.01 |
| 8 | 0.17 | 0.28 |
| 9 | 0.20 | 0.70 |

Although the invention has been described in considerable detail, it must be understood that such detail is for the purpose of illustration only and that many variations and modifications can be made by one skilled in the art without departing from the spirit and scope of the invention.

We claim:

1. A method for preventing polymerization of aqueous acrylamide contained in a vessel comprising passing an oxygen-containing gas through the aqueous acrylamide containing acrylonitrile and then contacting the resulting gas stream solely with a carbon adsorbent.

2. A method comprising contacting a vapor stream resulting from air sparging of aqueous acrylamide containing acrylonitrile with sufficient activated carbon adsorbent to substantially remove both acrylamide and acrylonitrile from the vapor stream.

3. The method of claim 2 wherein the activated carbon adsorbent is a gas-phase carbon.

4. The method of claim 3 wherein at least 90 percent of the acrylonitrile and acrylamide is removed.

5. The method of claim 4 wherein at least 99 percent of the acrylonitrile and acrylamide is removed.

6. The method of claim 2 wherein the aqueous acrylamide is contained in a vessel at a location remote from an acrylamide production or polymerization facility.

* * * * *